(12) United States Patent
Breton et al.

(10) Patent No.: US 11,034,992 B2
(45) Date of Patent: Jun. 15, 2021

(54) ASSAYS AND METHODS FOR DETECTING UDP-GLUCOSE

(71) Applicant: THE GENERAL HOSPITAL CORPORATION, Boston, MA (US)

(72) Inventors: Sylvie Breton, Boston, MA (US);
Rachel Liberman, Boston, MA (US);
Leileata M. Russo, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 191 days.

(21) Appl. No.: 16/087,968

(22) PCT Filed: Mar. 23, 2017

(86) PCT No.: PCT/US2017/023842
§ 371 (c)(1),
(2) Date: Sep. 24, 2018

(87) PCT Pub. No.: WO2017/165665
PCT Pub. Date: Sep. 28, 2017

(65) Prior Publication Data
US 2020/0071741 A1    Mar. 5, 2020

Related U.S. Application Data

(60) Provisional application No. 62/312,151, filed on Mar. 23, 2016.

(51) Int. Cl.
*C12Q 1/32* (2006.01)
*C12Q 1/54* (2006.01)

(52) U.S. Cl.
CPC ............ *C12Q 1/32* (2013.01); *C12Q 1/54* (2013.01)

(58) Field of Classification Search
CPC .................................... G01N 2333/91102
See application file for complete search history.

(56) References Cited

U.S. PATENT DOCUMENTS

| 4,791,057 A | 12/1988 | Misaki et al. |
| 5,306,413 A * | 4/1994 | Hayashi ............ C12Q 1/005 204/403.1 |
| 5,604,111 A | 2/1997 | Peck |
| 7,338,776 B2 | 3/2008 | Romero et al. |
| 7,473,244 B2 | 1/2009 | Frazier et al. |
| 2009/0260108 A1 | 10/2009 | Kitazawa et al. |
| 2010/0041123 A1 | 2/2010 | Minteer et al. |

FOREIGN PATENT DOCUMENTS

| ES | 2164609 B1 | 5/2003 |
| WO | 2000/068415 A2 | 11/2000 |
| WO | 2005/005629 A2 | 1/2005 |
| WO | 2015/070001 A2 | 5/2015 |

OTHER PUBLICATIONS

Turner, Aust. J. Biol. Sci., 1969, 22:1321-1327.*
Arthur et al., "Microanalysis of the metabolic intermediates of lactose synthesis in human milk and plasma using bioluminescent methods", Analytical Biochemistry 176(2) 449-456 (1989).
Goudsmit et al., "Enzymatic synthesis and interconversion of UDP-d-glucose and UDP-d-galactose in the albumen gland of the snail, *Helix pomatia*", Comparative Biochemistry and Physiology 54(1) 135-139 (1976).
Bassil et al., "UDP-glucose modulates gastric function through P2Y14 receptor-dependent and -independent mechanisms", Am J Physiol Gastointest Liver Physiol 296(4) G923-G930 (2009).
Huang et al., "Udp-glucose dehydrogenase as a novel field-specific candidate biomarker of prostate cancer", Int J Cancer 126(2) 315-327 (2010).
Pagni et al., "Assay for UDPglucose 6-dehydrogenase in phosphate-starved cells: gene tuaD of Bacillus subtilis 168 encodes the UDPglucose 6-dehydrogenase involved in teichuronic acid synthesis", Microbiology 145(Pt 5) 1049-1053 (1999).
Wu et al., "Stability of NADPH: effect of various factors on the kinetics of degradation", Clin Chem 32(2) 314-319 (1986).
Yamashita et al., "Biological functions of UDP-glucose synthesis in *Streptococcus* mutans", Microbiology 144(Pt 5) 1235-1245 (1998).
Lazarowski et al., "Release of cellular UDP-glucose as a potential extracellular signaling molecule." Molecular pharmacology 63.5 (2003): 1190-1197.

* cited by examiner

*Primary Examiner* — Bin Shen
(74) *Attorney, Agent, or Firm* — Nixon Peabody LLP; David S. Resnick; Mark J. FitzGerald

(57) ABSTRACT

Disclosed herein are methods, assays, compositions and kits for the detection and measurement of UDPglucose in biological samples. The methods, assays, compositions and kits are suitable for use with equipment that is readily available in a clinical laboratory, and permit rapid and reproducible detection and measurement of UDP-glucose at physiologically relevant levels in biological samples.

13 Claims, 6 Drawing Sheets

ASSAYS AND METHODS FOR DETECTING UDP-GLUCOSE

This application is a 35 U.S.C. § 371 National Phase Entry of the International Application No. PCT/US2017/023842 filed on Mar. 23, 2017, which designates the U.S. and which claims benefit under 35 U.S.C. § 119(e) of the U.S. provisional application No. 62/312,151 filed Mar. 23, 2016, the contents of each of which are incorporated herein by reference in its their entirety.

FIELD OF THE INVENTION

The field of the invention relates generally to the measurement of the metabolite and biomarker UDP-glucose.

BACKGROUND

Glucose can be stored in the form of glycogen in liver and/or muscle cells. Glycogen is a polymer of glucose residues, thus when the energy demands of a subject or tissue is high, glycogen can be broken down into glucose units for metabolism. Conversely, when the energy demands of the subject or tissue are low, glucose can be polymerized into glycogen for storage. Prior to glycogen formation, glucose is first converted to uridine diphosphate glucose (UDP-glucose), which is the immediate precursor for glycogen synthesis, through a series of enzymatic reactions.

UDP-glucose can also be used as a disease biomarker, for example, in the diagnosis of kidney injury, however a reproducible methodology that can be easily used in clinical laboratories is lacking in the art. The current gold standard method for measuring UDP-glucose uses an enzymatic reaction to radiolabel a byproduct of UDP-glucose, followed by High Performance Liquid Chromatography (HPLC). While this method is highly sensitive, reliable and specific, it is unsuitable for use in clinical settings as it uses dangerous materials, and cannot be performed in a timely manner in a clinical laboratory.

SUMMARY

Provided herein, in part, are methods, assays, and compositions for the detection and/or quantification of UDP-glucose, a biomarker of kidney injury and gastric cancer, among others. The methods, assays, and compositions provided herein can be used with equipment that is readily available in a clinical laboratory. In addition, the methods and assays described herein permit a rapid and reproducible result, such that diagnosis and treatment of a subject, particularly a hospitalized subject, can be started as soon as possible.

Provided herein, in one aspect, is a method for measuring the presence or amount of UDP-glucose in a sample, the method comprising: (a) contacting a liquid biological sample with an enzyme under conditions that permit the enzyme to catalyze the conversion of UDP-glucose in the sample to a byproduct, coupled with the stoichiometric conversion of NAD+ to NADH, and (b) measuring the level of NADH in the sample after step (a), thereby measuring the presence or amount of UDP-glucose in the biological sample.

In one embodiment of this aspect and all other aspects described herein, the enzyme is UDP-glucose dehydrogenase (UDPGD), which performs the following reaction: UDP-glucose+2NAD+→UDP-glucuronic acid+2NADH.

In another embodiment of this aspect and all other aspects described herein, NAD+ is added to the reaction of step (a).

In another embodiment of this aspect and all other aspects described herein, enzyme is immobilized.

In another embodiment of this aspect and all other aspects described herein, the enzyme is removed from contact with the liquid sample after step (a) and before step (b).

In another embodiment of this aspect and all other aspects described herein, the enzyme is immobilized in or on a solid support selected from the group consisting of: a cell culture plate, a multiwell plate, a disc, a bead, a woven paper, a filter paper, cardboard, a well, a plate, an electrode, a coated test strip, an uncoated test strip, a lateral flow strip, a lateral flow device, a dipstick device, a particle, and a magnetic particle.

In another embodiment of this aspect and all other aspects described herein, the method further comprises a step of removing protein(s) from the liquid biological sample.

In another embodiment of this aspect and all other aspects described herein, the step of removing protein(s) comprises filtration, solid phase extraction or liquid phase extraction.

In another embodiment of this aspect and all other aspects described herein, the method further comprises a step, before step (a), of removing endogenous NADH from the liquid biological sample, or from the liquid biological sample after protein removal.

In another embodiment of this aspect and all other aspects described herein, the step of removing endogenous NADH comprises heating under acidic conditions, or enzymatic degradation of endogenous NADH.

In another embodiment of this aspect and all other aspects described herein, the method further comprises titrating the biological sample to pH 8-9 prior to contacting with the enzyme.

In another embodiment of this aspect and all other aspects described herein, the method further comprises a step of removing NAD+, after step (a) and prior to step (b).

In another embodiment of this aspect and all other aspects described herein, the step of removing NAD+ comprises exposure of the sample to a strong base or an NAD+ nucleosidase.

In another embodiment of this aspect and all other aspects described herein, the method further comprises the steps of: (i) removing proteins from the liquid biological sample before step (b), (ii) removing endogenous NADH from the sample before step (a), (iii) titrating the sample to pH 8-9 for step (a), and (iv) treating the sample after step (a) to remove NAD+.

In another embodiment of this aspect and all other aspects described herein, the liquid biological sample is urine, blood, serum or sputum.

In another embodiment of this aspect and all other aspects described herein, NADH is measured using a luminescence assay, a colorimetric assay, a fluorescent detection technique, or absorbance at 340 nm.

In another embodiment of this aspect and all other aspects described herein, the NAD+ is on an assay substrate or in an assay vessel in dry form before addition of the biological sample.

In another embodiment of this aspect and all other aspects described herein, the assay substrate or assay vessel is selected from the group consisting of: a cell culture plate, a multiwell plate, a disc, a bead, a woven paper, a filter paper, cardboard, a well, a plate, an electrode, a coated test strip, an uncoated test strip, a lateral flow strip, a lateral flow device, a dipstick device, a particle, and a magnetic particle.

Also provided herein, in another aspect, is a method for measuring the presence or amount of UDP-glucose in a sample, the method comprising: (a) contacting a liquid biological sample with an enzyme under conditions that permit the enzyme to catalyze the conversion of UDP-glucose in the sample to a byproduct, coupled with the stoichiometric conversion of UDP-glucose into UDP and glycogen, and (b) measuring the level of UDP in the sample after step (a), thereby measuring the presence or amount of UDP-glucose in the biological sample.

In one embodiment, endogenous UDP can be removed prior to the generation of UDP as a read-out or surrogate marker by, e.g., enzymatic degradation. For example, background UDP levels can be cleared with the enzyme Gdalp from yeast, which converts UDP to UMP. See, e.g, Maria Dolores Lopez-Avalos, Daniela Uccelletti, Claudia Abeijon, and Carlos B. Hirschberg; The UDPase activity of the *Kluyveromyces lactis* Golgi GDPase has a role in uridine nucleotide sugar transport into Golgi vesicles. Glycobiology 2001; 11 (5): 413-422. doi: 10.1093/glycob/11.5.413; incorporated herein by reference. The yeast enzyme can be expressed in, e.g., *E. coli*.

In one embodiment of this aspect and all other aspects provided herein, the enzyme is glycogen synthase, which performs the following reaction: UDP-glucose+glycogen synthase→UDP+glycogen.

In another embodiment of this aspect and all other aspects described herein, the enzyme is immobilized.

In another embodiment of this aspect and all other aspects described herein, the enzyme is removed from contact with the liquid sample after step (a) and before step (b).

In another embodiment of this aspect and all other aspects described herein, the enzyme is immobilized in or on a solid support selected from the group consisting of: a cell culture plate, a multiwell plate, a disc, a bead, a woven paper, a filter paper, cardboard, a well, a plate, an electrode, a coated test strip, an uncoated test strip, a lateral flow strip, a lateral flow device, a dipstick device, a particle, and a magnetic particle.

In another embodiment of this aspect and all other aspects described herein, the method further comprises a step of removing protein(s) from the liquid biological sample prior to step (a).

In another embodiment of this aspect and all other aspects described herein, the step of removing protein(s) comprises filtration. Proteins can also be removed by, e.g., solid phase extraction, in which a solid phase protein binding reagent or matrix is added to the sample and then removed, e.g., by centrifugation, taking the proteins with it.

It is also noted that solid phase extraction can be used to concentrate UDP-glucose from a solution. For example, an affinity chromatography column, such as the column sold under the trade name ENVI-Carb™ SPE (Cat #57109-U; Sigma), could be used to concentrate all the nucleotide sugars present in a solution by binding them to a solid phase, eluting them with an organic solvent and drying the eluted nucleotide sugars (see, e.g., J. Barnes et al./MethodsX 3 (2016) 251-260, dx.doi.Org/10.1016/j.mex.2016.03.0102215-0161). The amount of UDP-glucose could then be measured by an enzymatic assay as described herein in the resulting smaller volume. It is contemplated that solid phase extraction can be performed using an automated clinical laboratory system such as the Biomek FX$^P$ Lab Automation Workstation from Beckman Coulter.

In another embodiment of this aspect and all other aspects described herein, the liquid biological sample is urine, blood, serum or sputum.

In another embodiment of this aspect and all other aspects described herein, the UDP is measured using an antibody or fragment thereof.

In another embodiment of this aspect and all other aspects described herein, the UDP is measured using an ELISA or lateral flow format.

Another aspect provided herein relates to an assay composition comprising: UDP-glucose dehydrogenase immobilized on a solid support.

In one embodiment of this aspect and all other aspects described herein, the solid support is selected from the group consisting of: a cell culture plate, a multiwell plate, a disc, a bead, a woven paper, a filter paper, cardboard, a well, a plate, an electrode, a coated test strip, an uncoated test strip, a lateral flow strip, lateral flow device, a dipstick device, a particle, and a magnetic particle.

In another embodiment of this aspect and all other aspects described herein, the composition is a dipstick or lateral flow strip or device.

In another embodiment of this aspect and all other aspects described herein, the dipstick or lateral flow strip or device comprises a test region buffered to pH 8-9.

In another embodiment of this aspect and all other aspects described herein, NAD+ is also provided on the solid support.

In another embodiment of this aspect and all other aspects described herein, the test region further comprises NAD+.

In another embodiment of this aspect and all other aspects described herein, the dipstick or lateral flow strip or device further comprises a region with a strong base or a region of immobilized NAD+ nucleosidase.

In another embodiment of this aspect and all other aspects described herein, the region of strong base comprises a high pH membrane.

In another embodiment of this aspect and all other aspects described herein, the region of strong base or the region comprising immobilized NAD+ nucleosidase is positioned following the test region in the direction of capillary flow in the dipstick or lateral flow strip or device.

In another embodiment of this aspect and all other aspects described herein, the dipstick or lateral flow strip or device further comprises a detection reagent that provides an optically detectable readout product in the presence of NADH.

In another embodiment of this aspect and all other aspects described herein, the detection reagent is nitro blue tetrazolium (NBT), a luciferin reagent, or a fluorescence detection agent.

In another embodiment of this aspect and all other aspects described herein, the detection reagent is positioned (i) following the test region and strong base region, (2) following the test region and region of immobilized NAD+ nucleosidase, or (3) directly after the test region in the direction of capillary flow.

In another embodiment of this aspect and all other aspects described herein, the dipstick or lateral flow strip or device comprises the following regions in order beginning at a sample application zone where the sample is applied and moving in the direction of capillary flow: (a) a test region comprising immobilized UDP-glucose dehydrogenase, (b) a region with a strong base or a region comprising immobilized NAD+ nucleosidase, and (c) a region comprising the detection reagent.

Another aspect provided herein relates to a dipstick or lateral flow strip or device as shown in FIG. 4.

Also provided herein in another aspect, is a kit comprising: UDP-glucose dehydrogenase, a solid support and instructions for use in an assay to detect UDP-glucose.

In one embodiment of this aspect and all other aspects described herein, the UDP-glucose dehydrogenase is immobilized on the solid support.

In another embodiment of this aspect and all other aspects described herein, the kit further comprises reagents to immobilize UDP-glucose dehydrogenase on or in a region of the solid support.

In another embodiment of this aspect and all other aspects described herein, the solid support is selected from the group consisting of: a cell culture plate, a multiwell plate, a disc, a bead, a woven paper, a filter paper, cardboard, a well, a plate, an electrode, a coated test strip, an uncoated test strip, a lateral flow strip or device, a dipstick device, a particle, and a magnetic particle.

In another embodiment of this aspect and all other aspects described herein, the lateral flow strip or device comprises a buffering composition at the UDP-glucose dehydrogenase region that buffers a biological sample contacted with that region to pH 8-9.

In another embodiment of this aspect and all other aspects described herein, the kit further comprises a reagent comprising a strong base.

In another embodiment of this aspect and all other aspects described herein, the strong base is 0.4N NaOH.

In another embodiment of this aspect and all other aspects described herein, the kit further comprises a detection reagent.

In another embodiment of this aspect and all other aspects described herein, the detection reagent comprises nitro blue tetrazolium (NBT), a luciferin reagent, or a fluorescence detection agent.

In another embodiment of this aspect and all other aspects described herein, the kit further comprises NAD+ nucleosidase.

In another embodiment of this aspect and all other aspects described herein, the kit further comprises a neutralizing reagent.

In another embodiment of this aspect and all other aspects described herein, the neutralizing reagent comprises an HCl/Trizma buffer.

Another aspect provided herein relates to a microtiter plate comprising immobilized UDP-glucose dehydrogenase.

In another embodiment of this aspect and all other aspects described herein, the plate further comprises lyophilized NAD+.

In another embodiment of this aspect and all other aspects described herein, the plate further comprises: (i) a standard curve present in wells of one row of the plate, wherein the standard curve comprises known quantities of UDP-glucose in each of the wells, (ii) a negative control well lacking enzyme, and/or (iii) a positive control well which is spiked with a known quantity of UDP-glucose.

Another aspect provided herein relates to a method of treating disease in a subject, the method comprising: (a) contacting a liquid biological sample obtained from a subject with an enzyme under conditions that permit the enzyme to catalyze the conversion of UDP-glucose in the sample to a byproduct, coupled with the stoichiometric conversion of NAD+ to NADH, and (b) measuring the level of NADH in the sample after step (a), thereby measuring the presence or amount of UDP-glucose in the biological sample, wherein a subject is treated with an agent when the levels of UDP-glucose are modulated relative to a reference sample, thereby treating the disease in the subject.

In one embodiment of this aspect and all other aspects provided herein, the levels of UDP-glucose are reduced relative to the reference sample.

In another embodiment of this aspect and all other aspects described herein, the levels of UDP-glucose are increased relative to the reference sample.

In another embodiment of this aspect and all other aspects described herein, the subject is a critically ill patient, an intensive care unit (ICU) patient, a septic patient, a patient with multi-trauma, a transplant patient, an outpatient, a patient suspected of having the disease, a cardio-thoracic surgery patient, a major surgery patient, or an emergency room patient.

In another embodiment of this aspect and all other aspects described herein, the disease is renal inflammation, chronic kidney disease, or acute kidney injury, asthma, cystic fibrosis, or chronic obstructive pulmonary disease.

In another embodiment of this aspect and all other aspects described herein, the renal inflammation is selected from the group consisting of: early stage renal inflammation, nephritis, acute tubular necrosis, glomerulonephritis, membranoproliferative glomerulonephritis, interstitial nephritis, IgA nephropathy, pyelonephritis, autoimmune disorders related chronic kidney disease, lupus nephritis, Goodpasture's syndrome and Wegener's granulomatosis.

In another embodiment of this aspect and all other aspects described herein, the reference level comprises: (a) an average level of UDP-glucose in a population of healthy subjects, (b) a range of levels of UDP-glucose in a population of healthy subjects, (c) two standard deviations above an average UDP-glucose level in a population of healthy subjects, (d) a first sample obtained from the subject prior to the onset of disease or as early as possible after the onset of disease (e.g., within one day, two days, three days, four days, five days, six days, seven days, eight days, nine days, 10 days or fewer from the onset of disease or, alternatively, from the initial presentation for clinical care), (e) a numeric value or range of values, or (f) a colored scale provided by a test strip or dipstick manufacturer for comparison of the color obtained by applying a sample to the test strip or dipstick.

In another embodiment of this aspect and all other aspects described herein, the disease is gastric cancer.

In another embodiment of this aspect and all other aspects described herein, the agent is a drug, a small molecule, a peptide, an antibody or fragment thereof, an engineered immune cell, an RNA interference agent, a nucleic acid, a protein, and/or supportive care.

Supportive care for acute kidney injury includes, for example, giving fluids for volume expansion, avoiding contrast agents or any other nephrotoxins, discontinuing antihypertensives, and increase blood pressure using medications such as norepinephrine by IV-infusion.

In another embodiment of this aspect and all other aspects described herein, the method further comprises: (i) measuring the level of NADH in a control well lacking enzyme, and/or (ii) measuring the level of NADH in a positive control well, which is spiked with a known quantity of UDP-glucose.

In another embodiment of this aspect and all other aspects described herein, the method is performed using an automated platform.

Definitions

A "subject," as that term is used herein includes humans and other primate subjects, such as monkeys and apes for veterinary medicine purposes; however, the technology is also contemplated for use with domestic animals, such as horses, pigs, sheep, cattle, and goats, as well as, companion animals, such as dogs and cats. The subjects can be male or female and can be of any suitable age, including infant, juvenile, adolescent, adult, and geriatric subjects. Non-limiting examples of subjects include critically ill patients, intensive care unit (ICU) patients, septic, multi-trauma and transplant patients.

The terms "sample", "biological sample", or "test sample" as used herein denote a sample taken or isolated from a subject or biological organism, e.g., an animal or human. Exemplary biological samples include, but are not limited to, a biofluid sample, a body fluid sample, blood (including whole blood), serum, plasma, urine, saliva, a biopsy and/or tissue sample etc. The term also includes a mixture of the above-mentioned samples. The term "sample" also includes untreated or pretreated (or preprocessed) biological samples. In some embodiments, the sample used for the assays and methods described herein comprises a urine sample. In some embodiments, the sample used for the assays and methods described herein comprises a serum sample collected from a subject to be tested. The term "liquid biological sample" refers to any biological sample derived from a patient that is in a liquid form at room temperature either as directly obtained from the subject (e.g., urine) or as a processed biological sample (e.g., serum, a centrifuged sample, or a homogenized tissue sample).

The test sample can be obtained by directly removing a sample from a subject, but can also be accomplished by using previously isolated samples (e.g., isolated at a prior time point and isolated by the same or another person). In addition, the test sample can be freshly collected or a previously collected sample. In some embodiments, the test sample can be an untreated test sample. As used herein, the phrase "untreated test sample" refers to a test sample that has not had any prior sample pre-treatment except for dilution and/or suspension in a solution. In some embodiments, a test sample can be a pre-processed test sample, for example, supernatant or filtrate resulting from a treatment selected from the group consisting of centrifugation, filtration, thawing, purification, titration of pH, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. In some embodiments, the test sample can be a frozen test sample, e.g., a frozen tissue. The frozen sample can be thawed before employing the methods and assays described herein. After thawing, a frozen sample can be centrifuged before being subjected to the methods and assays described herein. In some embodiments, the test sample is a clarified test sample, for example, by centrifugation and collection of a supernatant comprising the clarified test sample.

As used herein, the term "removing protein(s)," for example, from a liquid biological sample refers to the removal of all or a portion of the protein(s) present in the sample, particularly the removal of an adequate amount of protein such that the enzymatic reaction and/or detection of NADH or UDP, as required in a method as described herein, is not hindered or quenched. For example, the enzymatic reaction proceeds at a rate of at least 80%, at least 85%, at least 90%, at least 92%, at least 95%, at least 98%, at least 99% or even 100% of the rate of the enzymatic reaction in a substantially similar sample lacking detectable protein (other than the added enzyme). In another embodiment, the amount of NADH or UDP detected in a sample (e.g., a control sample) is at least 80%, at least 85%, at least 90%, at least 92%, at least 95%, at least 98%, at least 99% or even 100% of the NADH or UDP detected in a substantially similar sample lacking detectable protein (other than the added enzyme). In one embodiment, the term "removing protein(s)" refers to the removal of at least 50% of the protein(s) in the liquid biological sample. In other embodiments, the term "removing protein(s)' refers to the removal of at least 60%, at least 70%, at least 75%, at least 80%, at least 85%, at least 90%, at least 92%, at least 95%, at least 98%, at least 99%, or even 100% (e.g., all of the detectable protein) of the protein in the liquid biological sample. It will be appreciated by one of skill in the art that the amount of protein in the sample will depend on the liquid biological sample obtained from a subject. For example, whole blood or serum each has higher protein content than that of urine (depending on the degree of kidney disease). Thus, the removal of protein(s) may be required when using certain liquid biological samples while it is not required for other liquid biological samples. In addition, the amount of protein to be removed from each sample in order to maintain the linear properties of the enzymatic reaction and/or to permit NADH or UDP detection will depend on the characteristics and protein content of the liquid bacterial sample. As used herein, the term "removing endogenous NADH" refers to the removal of all or part of the NADH that is present in an untreated liquid biological sample or a liquid biological sample that has been deproteinated. In some embodiments, the term "removing endogenous NADH" refers to the removal of at least 60%, at least 70%, at least 75%, at least 80%, at least 85%, at least 90%, at least 92%, at least 95%, at least 98%, at least 99%, or even 100% (e.g., all) of the detectable NADH in the liquid biological sample. In other embodiments, the term "removing endogenous NADH" refers to the removal of NADH such that the background NADH level in a control sample lacking enzyme is less than 20% of the total NADH level in a substantially similar sample comprising the enzyme (i.e., background NADH+ NADH generated by the enzymatic reaction); in other embodiments, the background NADH level in a control sample lacking enzyme is less than 15%, less than 10%, less than 9%, less than 8%, less than 7%, less than 6%, less than 5%, less than 4%, less than 3%, less than 2%, less than 1%, less than 0.5%, less than 0.1% or even 0 (e.g., none) of the total NADH level in a substantially similar sample comprising the enzyme. One of skill in the art will appreciate that the amount of endogenous NADH does not need to be zero, as one can simply normalize the samples by subtracting the background NADH from the total NADH (background NADH+NADH generated in reaction) in each sample to permit accurate quantification of NADH levels. However, it will also be appreciated by one of skill in the art that such endogenous NADH levels should be low enough that subtle differences in total NADH measured between samples is not obscured by an overly large contribution from endogenous NADH. In one embodiment, endogenous NADH is degraded by exposure of a sample to the enzyme xanthine oxidase, which converts NADH to NAD+. When this approach is used, xanthine oxidase should be removed or inactivated before proceeding to the assay steps that use NADH as a read-out or surrogate indicator molecule. In an alternative embodiment, endogenous NADH is not removed before assaying for UDP-glucose, but rather, a "blank" reaction is run on the test sample in which no UDPGD enzyme is added, and the signal is subtracted from the signal in the test samples that receive the UDPGD enzyme.

As used herein, the term "heating under acidic conditions" refers to a step of substantially simultaneously treating a sample with an acid and heating the sample, such that the step effectively removes or degrades endogenous NADH, as that term is used herein. In some embodiments, the acid comprises a pH equal to or: less than 7, less than 6, less than 5, less than 4, less than 3, less than 2, less than 1, or even a pH of 0. In some embodiments, the sample is heated to at least 25° C., at least 30° C., at least 32° C., at least 35° C., at least 40° C., at least 50° C., at least 55° C., at least 60° C., at least 65° C., at least 70° C., at least 75° C., at least 80° C., at least 90° C., at least 95° C., at least 100° C. or more. Every pairwise combination of acid and temperature are contemplated herein, for example, an acid having a pH 7/55° C.; pH 6/55° C., pH 5/55° C., pH 4/55° C., pH 3/55° C., pH 2/55° C., pH 1/55° C.; pH 0/55° C., or conversely a pH 3/25° C.; pH 3/30° C.; pH 3/32° C.; pH 3/35° C.; pH 3/40° C.; pH 3/50° C.; pH 3/55° C.; pH 3/60° C.; pH 3/65° C.; pH 3/70° C.; pH 3/75° C.; pH 3/80° C.; pH 3/90° C.; pH 3/95° C.; pH 3/100° C. etc.

As used herein, the term "strong base" refers to a reagent comprising a pH capable of degrading at least 90% of the unreacted NAD+ present in the sample after the enzymatic reaction is complete, thereby minimizing the amount of background NAD+ that may interfere with the accurate measurement of NADH and provided that the strong base does not degrade NADH. In other embodiments, the strong base is capable of degrading at least 92%, at least 95%, at least 98%, at least 99%, at least 99.9%, or even 100% (e.g., all detectable unreacted NAD+) of the unreacted NAD+ in the sample. In other embodiments, the strong base comprises a pH of at least 9.5, at least 10, at least 10.5, at least 11, at least 11.5, at least 12, at least 12.5, at least 13, at least 13.5, or even 14. In one embodiment, the strong base is lithium hydroxide (LiOH), sodium hydroxide (NaOH), potassium hydroxide (KOH), rubidium hydroxide (ROH), cesium hydroxide (CsOH), magnesium hydroxide in solution (Mg(OH)$_2$), calcium hydroxide (Ca(OH)$_2$), strontium hydroxide (Sr(OH)$_2$), or barium hydroxide (Ba(OH)$_2$). In one embodiment, the strong base is 0.4N NaOH.

A "lateral flow" device or strip refers to a strip of capillary beds (e.g., porous paper, microstructured polymer, or sintered polymer) or a device comprising such a strip, whereby the capillary beds of the lateral flow strip transports fluid (e.g., a liquid biological sample) spontaneously. With respect to the methods and assays described herein, a lateral flow strip or device comprises one or more regions through which the fluid (e.g., liquid biological sample) migrates in a desired order, wherein the first region (e.g., the test region) is the region closest to a sample application zone in the direction of capillary flow. Other regions contemplated herein in a lateral flow device can include a test region, a region of strong base or a region comprising immobilized NAD+nucleosidase, and/or a detection region, as those terms are used herein.

As used herein, the term "sample application zone" refers to the region of a lateral flow strip or device that is contacted with the fluid sample. The sample application zone may be external to the device, while the other regions may be internal to the device to avoid damage, for example, to the test region. The sample application zone can store excess fluid from the sample. Once the fluid is contacted with the sample application zone, the fluid is moved via the capillary beds to the next desired region of the lateral flow device in the direction of capillary flow. Although not a requirement, the sample application zone is generally located at one terminal end of a lateral strip or device.

As used herein, the term "direction of capillary flow" refers to the direction in which the fluid migrates through a lateral flow strip or device beginning at the sample application zone and migrating through the remaining lateral flow strip or device by capillary flow.

As used herein, the term "test region" refers to a region of the lateral flow strip or device in which an enzymatic reaction that generates NADH or UDP as described herein occurs. Thus, in some embodiments, the test region comprises immobilized enzyme (e.g., UDP-glucose dehydrogenase) and/or lyophilized NAD+. In another embodiment, the test region is buffered to a pH of 8-9. The test region will also comprise components necessary to provide conditions that permit the enzyme to catalyze the desired chemical reaction. The test region can also include, for example, a salt-sugar matrix that is dissolved when the fluid reaches the test region and permits the components of the liquid biological sample to mix with the reaction components of the test region. Typically, as the fluid moves through the test region, the enzymatic reaction occurs; thus the length of the test region should be long enough to permit adequate enzymatic catalysis to generate detectable levels of NADH (e.g. in the linear portion of the reaction).

As used herein, the term "region of strong base" refers to a region on a lateral flow strip or device comprising a strong base or a high pH (e.g., a pH membrane) that facilitates the degradation of unreacted NAD+ in the sample as it is carried through the lateral strip or device by capillary flow.

As used herein, the term "region of immobilized NAD+ nucleosidase" refers to a region on a lateral flow strip or device comprising a quantity of immobilized NAD+ nucleosidase that facilitates the degradation of unreacted NAD+, which is carried through the lateral strip or device by capillary flow. The NAD+ nucleosidase region will also comprise components necessary to provide conditions that permit the enzyme to catalyze the degradation of unreacted NAD+. The NAD+ nucleosidase region can also include, for example, a salt-sugar matrix that is dissolved when the fluid reaches the NAD+ degradation region and permits the components of the sample to mix with the reaction components of the region comprising immobilized NAD+ nucleosidase. Typically, as the fluid moves through the region comprising the NAD+ nucleosidase, degradation of unreacted NAD+ occurs, thus the length of the region should be long enough to permit adequate degradation of unreacted NAD+ (e.g., degradation of at least 90% of the unreacted NAD+) in the sample. In one embodiment, the pH of the region of immobilized NAD+ nucleosidase is a pH that permits optimal enzymatic activity to degrade NAD+. In another embodiment, the region of immobilized NAD+ nucleosidase comprises a pH that is substantially similar to the pH of the test region.

As used herein, the term "region comprising a detection reagent" refers to to a region of a lateral flow strip or device comprising an optically detectable readout product that can detect NADH, for example, by reduction of a dye or chemical to produce the optically detectable readout product. In one embodiment, a lateral flow device as used herein further comprises a housing in which the sample application zone is the only zone that protrudes from the housing, for example, to protect the remaining zones during application of urine by the subject. Alternatively, the device can be a dipstick or lateral flow solid support that does not require a housing; this type of lateral flow device can be used in a clinical setting where the splash-guard provided by the housing is not required as the sample application zone is simply dipped into the sample.

In one embodiment, the region comprising a detection reagent should be visible in the housing of a lateral flow device, for example, through a window in the device. As used herein, the term "buffering composition" refers to a reagent that resists a change in pH when contacted with a sample, such that the combination of the sample+buffering composition retains a substantially similar pH as the buffering compositions alone. For example, a buffering composition having a pH of 8-9 will retain a pH of 8-9 when contacted with a sample (e.g., a physiological sample).

As used herein, the term "detection reagent" refers to a reagent or molecule which can be used to provide a detectable (preferably quantifiable) signal when contacted with an analyte or byproduct such as NADH or UDP. Detection reagents can provide signals detectable by fluorescence, enzyme activity, radioactivity, colorimetry, gravimetry, X-ray diffraction or absorption, magnetism, binding affinity, hybridization radiofrequency, nanocrystals and the like. In some embodiments, the detection reagent comprises a dye (e.g., nitro blue tetrazolium (NBT)), a luciferin reagent or a fluorescent reagent. "Qualitative or quantitative" detection refers to visual or automated assessments based upon the magnitude (strength) or number of signals generated by the label.

As used herein, the term "neutralizing reagent" refers to a reagent having a pH that effectively negates the pH of an acid or base in a sample (e.g., a sample contacted with a strong base), thus the resulting reaction mixture (e.g., sample+neutralizing reagent) comprises a neutral or near neutral pH (e.g., pH 6, pH 7, pH 8, pH 6-8, pH 6-7, pH 7-8 etc.)

As used herein, the term "analyte" generally refers to a substance to be detected. For instance, analytes may include metabolic substances, byproducts of an enzymatic reaction, antigenic substances, haptens, antibodies, and combinations thereof. Analytes include, but are not limited to, biochemical compounds, metabolic byproducts, organic compounds, proteins, peptides, amino acids, nucleic acids, hormones, steroids, vitamins, drugs or drug intermediaries or byproducts. Specific examples of some analytes include UDP-glucose, UDP, NADH, UDP-glucuronic acid, etc.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean ±1%.

BRIEF DESCRIPTION OF THE FIGURES

FIG. 3A is a line graph showing the measurement of UDP-glucose, with little variability, between days. FIG. 3B is a line graph showing the measurement of UDP-glucose, which is reproducible by an external and independent laboratory.

DETAILED DESCRIPTION

Figure 1:
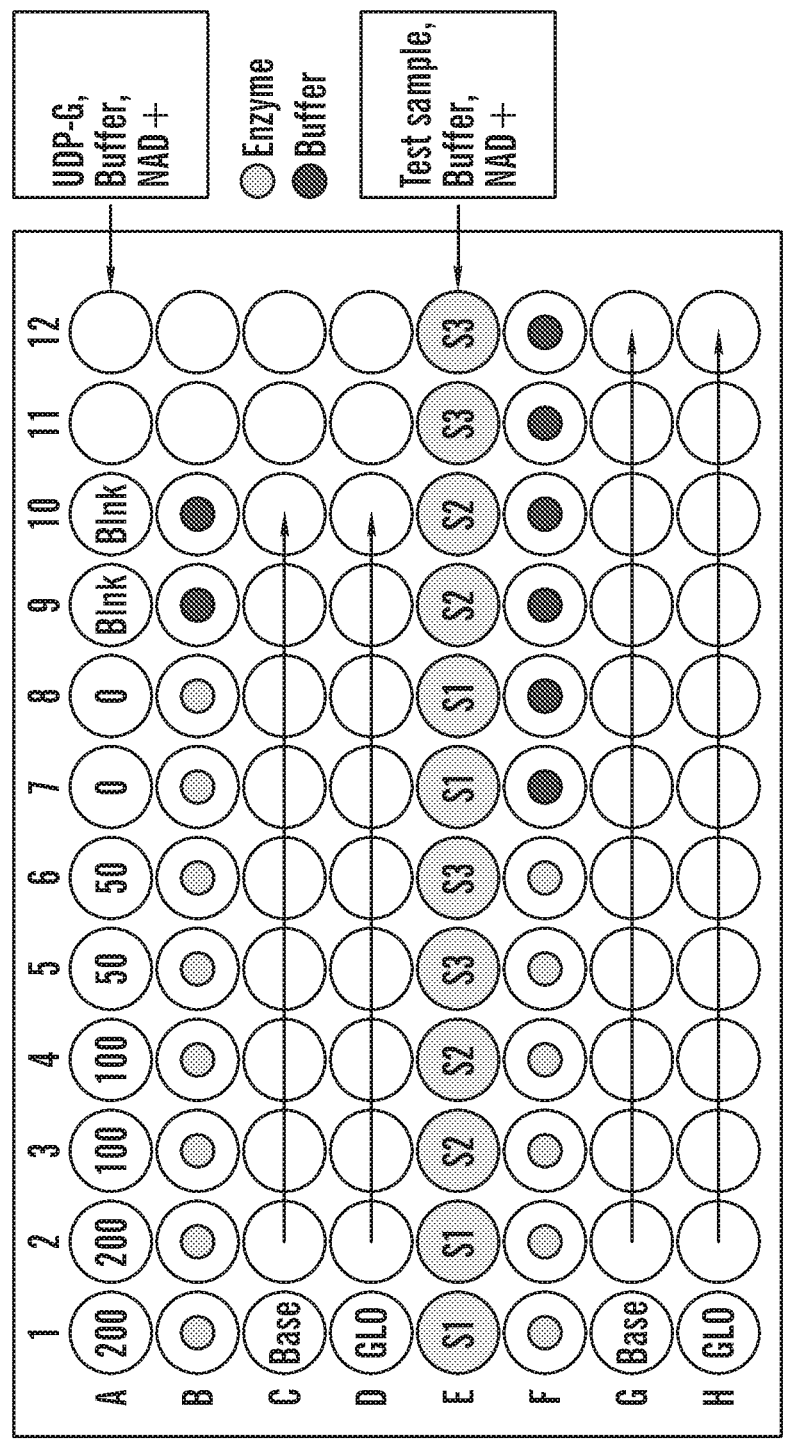
FIG. 1 is a schematic showing one example of a 96-well plate set-up for the measurement of UDP-glucose, for example, by measuring the release of NADH from a reaction coupled by UDP-glucose dehydrogenase.
Figure 2:
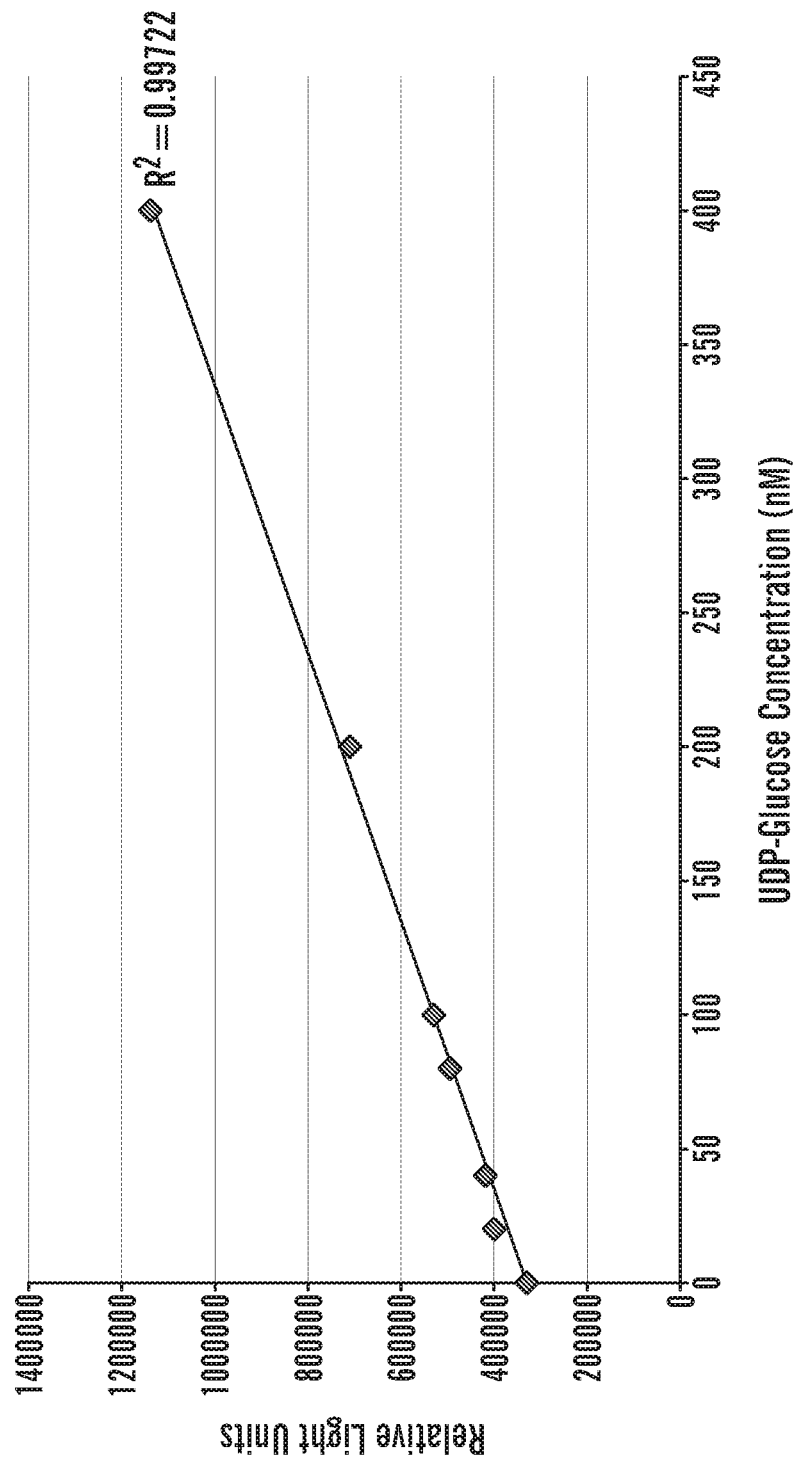
FIG. 2 is a line graph showing the measurement of known UDP-glucose concentrations in urine at physiological pH.

Provided herein are methods and assays for the detection and/or quantification of UDP-glucose (UDPG). Prior to the assays disclosed herein, the reliable, rapid measurement of UDP-glucose at physiological and pathophysiological concentrations presented many technical challenges. For example, UDPG cannot be measured directly by high performance liquid chromatography (HPLC) because HPLC differentiates molecules by size, and UDPG is the same size as the related compound, UDP-galactose. Finally, pathophysiological concentrations of UDPG in body fluids (e.g., urine) are in the nanomolar range. The methods and assays described herein are suitable for measurement of nanomolar concentrations of UDPG and are fast, reliable, user friendly and can be performed in a clinical laboratory setting.

Assays and Methods

Provided herein are methods, assays and kits relating to the detection of UDP-glucose in a liquid biological sample, by coupling a reaction converting UDP-glucose to a byproduct with the stoichiometric production of NADH or UDP. Exemplary protocols for the assays and methods described herein can be found in the working Examples. The general premise of the assays and variations thereof are described briefly below.

When NADH is to be measured as the read-out molecule, the first step of the assay, which is optional, can be a pre-processing step to remove proteins that can interact with NADH from a liquid biological sample. Another pre-processing step, which is also optional, includes the removal of high endogenous levels of NADH from the liquid biological sample (e.g., enzymatically or by heating), as high levels of endogenous NADH can inhibit the reaction and potentially mask the results. As a threshold, an NADH level of 2 micromolar ($\mu$M) or greater is considered to be "high" as the term is used herein. As an alternative to the removal of endogenous NADH, a control or blank reaction lacking exogenous enzyme can be run and endogenous NADH detected to permit the endogenous level to be subtracted out.

Next, the fluid sample (pre-treated sample or a liquid biological sample) should be buffered to pH 8-9—this step was found to facilitate the detection of threshold levels of UDP-glucose with this assay. In one embodiment, pH is buffered to pH 8.0.

The enzyme UDPG dehydrogenase is added to the reaction along with the co-factor NAD+. During the reaction UDPG is converted to UDP-glucuronic acid, and a stoichiometric amount of NAD+ is converted to NADH. NADH is then measured and its concentration is used to deduce the starting UDPG concentration. Because of the low concentration of UDPG present in body fluids (e.g., nanomolar range), it is not possible to measure NADH directly by absorbance at 340 nM. The assays and methods described herein overcome the major challenge of detecting nanomolar concentrations of NADH without interference by the co-factor NAD+. Commercial kits currently exist for detection of low concentrations of NADH by amplification, but the amplification step converts NAD+ back to NADH. Because NAD+ is added for the first reaction step of the assays and methods described herein that rely upon NADH generation, the interconversion between NAD+ and NADH would negate the NADH generation step and all samples would appear to have the same NADH concentration (i.e., equal to the starting NAD+ concentration). One approach to solve this challenge is to heat the reactants in a strong base before steps for the detection of NADH. This treatment decomposes NAD+ but leaves NADH unaffected.

A second issue is presented by the use of UDPG dehydrogenase for the assay. Namely, at low levels of NAD+, the enzyme begins to catalyze the reverse reaction i.e., converting the NADH generated back to NAD+. To solve this challenge, UDPG dehydrogenase is removed after the initial reaction, thereby preventing the reverse reaction. Any of a number of ways can be used to remove or inactivate the added enzyme. However, a straight-forward approach is to immobilize the enzyme on the bottom of the reaction well. Removal of the enzyme is then easily accomplished by transferring the reaction mixture to another vessel, e.g., a well lacking immobilized enzyme, or an NADH detection device. The nanomolar concentrations of NADH can then be measured using different modalities including, for example, a commercial glo-assay, which uses luminescence as a readout for NADH. An alternative to this method which removes enzyme is to provide NAD+ in excess, thereby driving the reaction in the direction of NADH production. If so desired, excess NAD+ can be later removed from the resulting sample as described elsewhere herein.

It will be recognized by one of skill in the art that the reaction converting UDP-glucose to a byproduct is performed such that the amount of substrate (e.g., NAD+) and the resulting rate of the enzymatic reaction occurs in the substantially linear portion of the curve representing e.g., Michaelis-Menten enzyme kinetics, thereby reducing variability among samples that can be seen as the enzyme kinetics curve reaches a maximal rate. The use of Michaelis-Menten kinetics plots the substrate concentration vs. the reaction rate; an ideal Michaleis-Menten plot comprises a curve having an initial, substantially linear rate, and a maximal rate. The maximal rate occurs when the addition of a higher concentration of substrate does not cause an increase in the reaction rate. Thus, in one embodiment, the amount of substrate and the reaction rate for each enzyme is optimized for the assays and methods described herein using Michaelis-Menten kinetics, such that the amount of substrate and/or reaction rate occurs in a substantially linear portion of the Michaelis-Menten graph.

In one embodiment, excess NAD+ is added to the reaction, along with enzyme in excess, such that UDP-glucose is limiting. For example, NAD+ can be added to a concentration of 2 mM per well, and 0.04 units of enzyme added per well to achieve an excess of both. One unit of enzyme is the amount of UDP-glucose dehydrogenase required to oxidize 1.0 □mole of UDP-glucose to UDP-glucuronic acid per minute at pH 8.7 at 25° C.

Alternatively, the complete reaction curve can be determined for each sample and the data fit to a non-linear rate equation (e.g., "progress-curve analysis"). This is particularly useful when the slope of the linear region of the Michaelis-Menten kinetics curve for a desired enzyme is very steep (e.g., when the initial rate is too fast to measure accurately) or when an excess of substrate (e.g., NAD+) is used in the reaction mix.

Biological Samples

A biological sample can be obtained from any organ or tissue in the individual to be tested, provided that the biological sample is obtained in a liquid form or can be pre-treated to take a liquid form. Typically the biological sample will comprise a urine sample, blood sample, a sputum sample (e.g., lung secretions), or a serum sample, however other biological samples are contemplated herein, for example, cerebrospinal fluid.

In some embodiments, a biological sample is treated to remove cells or other biological particulates. Methods for removing cells from a blood or other biological sample are well known in the art and can include e.g., centrifugation, sedimentation, ultrafiltration, immune selection, etc. Some non-limiting examples of biological samples include a blood sample, a urine sample, a serum sample, a semen sample, a sputum sample, a lymphatic fluid sample, a cerebrospinal fluid sample, a plasma sample, a pus sample, an amniotic fluid sample, a bodily fluid sample, a stool sample, a biopsy sample, a needle aspiration biopsy sample, a swab sample, a mouthwash sample, a cancer sample, a tumor sample, a tissue sample, a cell sample, a synovial fluid sample, or a combination of such samples. The biological sample can also be a solid or semi-solid sample, such as a tissue or stool sample, that has been treated to take a liquid form by, for example, homogenization, sonication, pipette trituration, cell lysis etc. For the methods described herein, it is preferred that a biological sample is from urine, serum, whole blood, or sputum.

In some embodiments, samples can be obtained from an individual with a disease or pathological condition. In one embodiment, the disease or pathological condition is renal inflammation and/or gastric cancer. Some exemplary disease or pathological conditions include, but not limited to: a blood disorder, a lung disorder (e.g., asthma, cystic fibrosis, or chronic obstructive pulmonary disease), blood lipid disease, autoimmune disease, a cardiovascular disorder, endocrine disorder, muscle wasting and whole body wasting disorder, kidney disease, stroke, diabetes (e.g., Type I or Type II diabetes), disorders associated with diabetes (e.g., PVD), hypertension, liver disease, pancreatic disease, gastrointestinal diseases (including diseases of the colon, diseases of the spleen, appendix, gall bladder, and others) and the like. For further discussion of human diseases, see Mendelian Inheritance in Man: A Catalog of Human Genes and Genetic Disorders by Victor A. McKusick (12th Edition (3 volume set) June 1998, Johns Hopkins University Press, ISBN: 0801857422), the entirety of which is incorporated herein.

Preferably, samples from a normal demographically matched individual and/or from a non-disease sample from a patient having the disease are used in the analysis to provide controls. The samples can be obtained from individuals sharing a desired trait, for example, gender, age, pathology, predisposition to a pathology, kinship, death from the same disease, treatment with the same drug, exposure to chemotherapy, exposure to radiotherapy, exposure to hormone therapy, exposure to surgery, the same genetic alteration or group of alterations, expression of the same gene or sets of genes (e.g., samples can be from individuals sharing a common haplotype, such as a particular set of HLA alleles), and the like.

In one embodiment, a reference or control sample is obtained from the subject being analyzed for UDP-glucose level, e.g., upon presentation in a clinical setting, before treatment is commenced. Alternatively, changes in UDP-glucose levels indicative of therapeutic progress can be measured against levels detected earlier in the course of treatment.

Lateral Flow Devices

Contemplated herein are lateral flow assays adapted for use in the detection of NADH or UDP, as described herein. Such lateral flow assays permit the flow of a liquid sample, applied to the sample application zone, to deliver the sample/reactants to a test region (e.g., a reaction zone) of the lateral strip or device, and then the sample with a generated byproduct is delivered to a detection zone, which provides a read-out (e.g., visual, optical, fluorescent, etc.). As one example, provided herein is an assay that uses reduction of nitro blue tetrazolium (NBT) by NADH to generate a colored product at a test region. As samples with generated NADH flow over a region with NBT (no color), the NBT is reduced to the blue form, which is visible on a strip.

In one embodiment, where NBT is used to generate a detectable product, a reductase, including, but not limited to a diaphorase can be immobilized (e.g., via adsorption or via immunocapture) on the dipstick or test strip. As the NADH-containing solution flows through the region with the reductase enzyme, the NADH is oxidized and would reduce the NBT to the colored precipitate NBTH.

In one embodiment, the levels of NADH or UDP in a sample can be detected by a lateral flow assay test (LFA), or strip test. LFAs are a simple device intended to detect the presence (or absence) of an analyte, e.g. NADH or UDP, in a fluid sample. With a lateral flow method, a spatial separation is defined in the strips between the sample application zone and detection region. Most conventional lateral flow strips are designed for test samples that are readily available in large quantities (e.g., urine).

While for simplicity the description refers to lateral flow immunoassays, it should be understood that lateral flow immunoassays can also be adapted for the measurement of an analyte without the use of antibody. Both lateral flow immunoassays (e.g., using a UDP-glucose antibody) and lateral flow analyte assays (e.g., detection of NADH to measure UDP-glucose levels) are contemplated for use herein.

LFAs are an assay in which the test sample flows along a solid substrate via capillary action. After the sample is applied to the lateral flow strip it encounters a test region where an enzymatic reaction coupled to NADH or UDP production occurs and continues to a region comprising a detection reagent that permits visualization or detection of NADH or UDP. The fluid can optionally go through one or more different regions on the lateral flow strip following the test region and prior to the detection region.

LFAs are essentially assays adapted to operate along a single axis to suit the test strip format or a dipstick format and most often proceed from sample application to readout without additional steps by the user. That is, sample application generally leads to an assay result with the further user input. Other lateral flow configurations may include one or more steps by the user after sample application, e.g., insertion into a detector device (e.g., a luminometer, fluorescence detector, etc.) or sometiems, addition of another reagent. Strip tests are extremely versatile and can be easily modified by one skilled in the art for detecting an enormous range of antigens or analytes from fluid samples such as urine, blood, water samples etc. Strip tests are also known as "dipstick tests," the name bearing from the literal action of "dipping" the test strip into a fluid sample to be tested. LFA strip tests are easy to use, require minimum training and can easily be included as components of point-of-care test (POCT) diagnostics to be used on site in the field.

A typical test strip can comprise one or more of following components: (1) sample application zone comprising e.g., an absorbent pad (i.e., the matrix or material) onto which the test sample is applied; (2) test region comprising immobilized enzyme; (3) a test results area comprising a detection reagent or reaction membrane—such as a hydrophobic nitrocellulose or cellulose acetate membrane onto which, for example, a detection reagent is immobilized in a line across the membrane as a capture zone or test line (a control zone may also be present, containing NADH or another reducing agent, for example, that reduces NBT to generate a blue color) or an antibody reagent; and (4) optional wick or waste reservoir—a further absorbent pad designed to draw the sample across the detection reagent zone or reaction membrane by capillary action and collect it. In addition, lateral flow strips as described herein can further comprise one or more of the following: a region comprising a strong base or a region comprising immobilized NAD+ nucleosidase to degrade unreacted NAD+.

The components of the strip can be fixed to an inert backing material and can be presented in a simple dipstick format or within a plastic casing with a sample port and reaction window showing the test read-out/capture and control zones. While not strictly necessary, most tests will incorporate a second, coated line which contains an antibody or other reagent that picks up free read-out substrate (e.g., free latex or gold particles) in order to confirm the test has operated correctly.

The use of "dip sticks" or LFA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U. S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. Given the reaction description and considerations described herein, it is within the skill of one in the art to modify the teachings regarding "dip stick" technology for the detection of NADH or UDP using e.g., dye, luciferin or fluorescent reagents as described herein.

Figure 6:
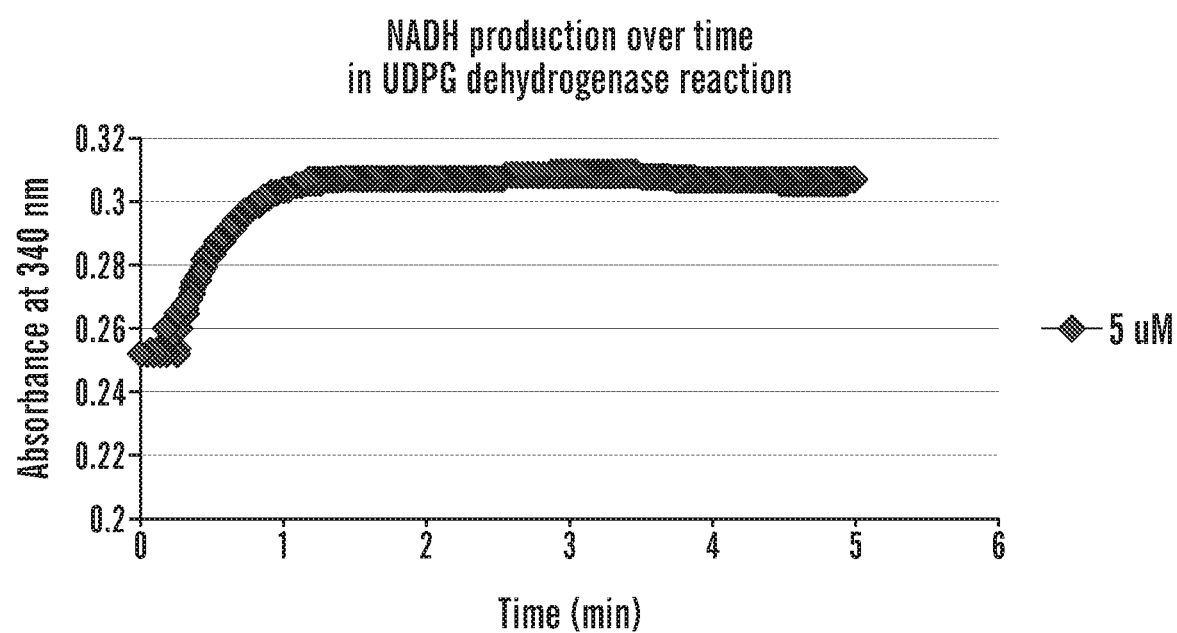
FIG. 6 is a line graph showing NADH production over time in the UDP-glucose dehadrogenase mediated reaction with UDP-glucose.
Figure 7:
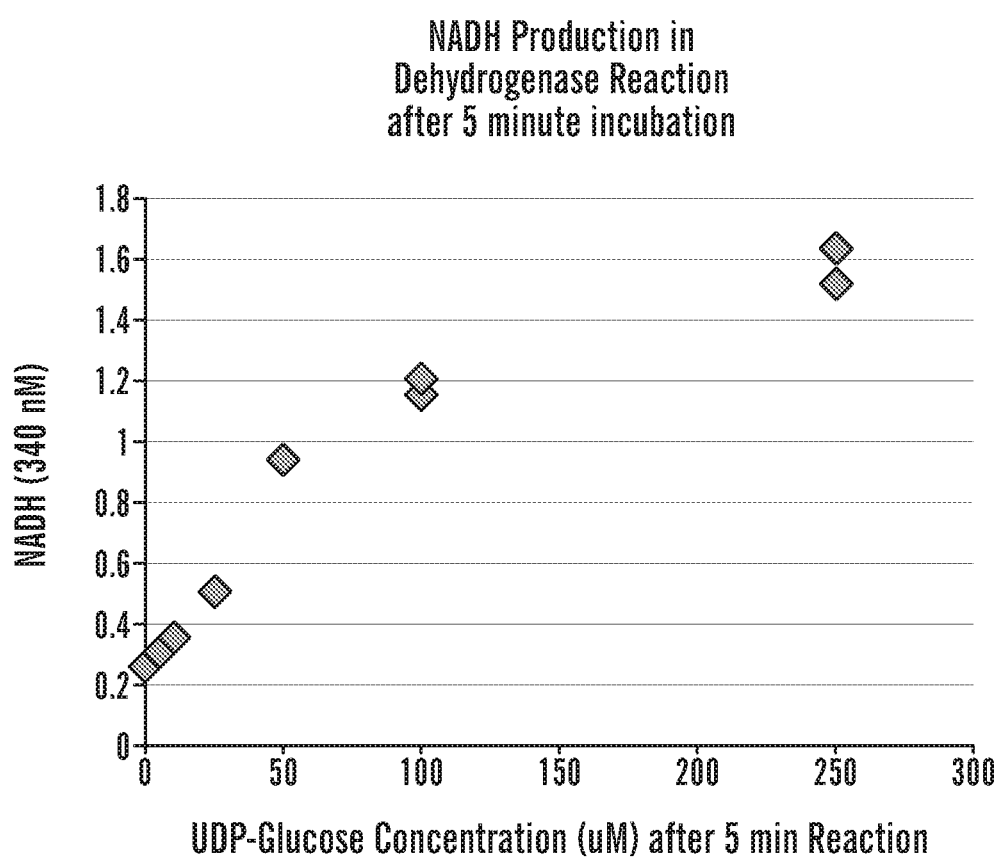
FIG. 7 is a plot of NADH production in a UDP-glucose dehydrogenase reaction in five minutes with varying initial concentrations of UDP-glucose. The reaction remains linear in this time frame for UDP-glucose concentrations up to at least 100 nM.

In one embodiment, the reaction to generate a stoichiometric amount of NADH from the reaction of UDP-glucose with UDPGD is incubated for a matter of minutes, e.g., 5 or 10 minutes, in the liquid assay format in order to generate sufficient amounts of NADH for detection. This extended time is not as readily achieved in the dipstick or lateral flow format. However, options to overcome this include, in one embodiment, performing the first enzymatic reaction in an assay well for a prescribed period of time before inserting a dipstick or applying sample to a test strip. Alternatively, if all reactions took place on the dipstick or test strip, a shorter incubation should not present a problem because most of the enzyme reaction actually takes place within the first minute (FIG. 6), although the reaction continues to remain linear after a 5 minute incubation, after the initial linear velocity for low (physiological) concentrations of UDP-glucose (up to 100 µM; FIG. 7).

A urine dipstick is a conventionally a colorimetric chemical assay comprising a reagent stick-pad, which is immersed in a fresh urine specimen and then withdrawn. Alternatively, the urine sample can be applied directly to the sample application zone by the subject (e.g., analogous to a pregnancy test). After predetermined times the colors of the reagent pad are compared to standardized reference charts. The urine dipstick offers an inexpensive and fast method to perform screening urinalyses, which help in identifying the presence of various diseases or health problems. A urine dipstick provides a simple and clear diagnostic guideline and can be used in the methods and kits as described herein. Accordingly, one aspect of the present technology relates to a method for detecting NADH or UDP using a device, such as a dipstick, as described herein. When the sample is not clear, e.g., blood or other sample types, a centrifugation or filtration step to render a clear sample may be applied so as to avoid pigment or other entities from fouling the optical read-out.

In some cases, the lateral flow strip may also comprise a control that gives a signal to the user that the assay is performing properly. For instance, the control zone can contain an immobilized receptive material that is generally capable of forming a chemical and/or physical bond with probes or with the receptive material immobilized on the probes. Some examples of such receptive materials include, but are not limited to, antigens, haptens, antibodies, protein A or G, avidin, streptavidin, secondary antibodies, and complexes thereof. In addition, it may also be desired to utilize various non-biological materials for the control zone receptive material. For instance, in some embodiments, the control zone receptive material can also include a polyelectrolyte that may bind to uncaptured probes. Because the receptive material at the control zone is only specific for probes, a signal forms regardless of whether the analyte is present. The control zone can be positioned at any location along the test strip, but is preferably positioned downstream from the detection zone.

In one embodiment, detection involves reduction of nitro blue tetrazolium by NADH present and/or generated during the assay. In this embodiment, the control line can include a line of NBT spatially downstream of the test line and immediately downstream of a line or zone of dried reducing agent. Flow of sample past the test line will liberate the reducing agent and carry it to the control line of NBT, which will be reduced to generate a control line indicating the sample reactants have successfully reacted at that point.

Qualitative, semi-quantitative, and quantitative results can be obtained with the lateral flow device(s) described herein. For example, when it is desired to semi-quantitatively or quantitatively detect an analyte, the intensity of any signals produced at the region comprising a detection reagent may be measured with e.g., an optical reader. The actual configuration and structure of the optical reader may generally vary as is readily understood by those skilled in the art. For example, optical detection techniques that can be utilized include, but are not limited to, luminescence (e.g., fluorescence, phosphorescence, etc.), absorbance (e.g., fluorescent or non-fluorescent), diffraction, etc. Further optical methods include but are not limited to, measuring light scattering, simple reflectance, luminometer or photomultiplier tube; radioactivity (measured with a Geiger counter, etc.); electrical conductivity or dielectric (capacitance); electrochemical detection of released electroactive agents, such as indium, bismuth, gallium or tellurium ions.

Once the amount of detection agent has been quantified, the amount can then be mapped onto another measurement scale. For example, while the result of the assay can be measured as a density of reflectance (Dr), the result reported can be more meaningful in other units, such as RI (intensity relative to that of a control zone or background level). Results can also be expressed as the number of copies of analyte present in the measurement volume.

Lateral Flow Immunoassays

In one aspect, the lateral flow device is configured for a lateral flow immunoassay (LFIA). In this aspect, antibodies that bind a target analyte are used in a competitive or sandwich immunoassay adapted to the lateral flow format.

Conventional sandwich LFIAs are similar to sandwich ELISAs. The sample first encounters and mobilizes colored particles which are labeled with antibodies raised to the target antigen. The test line will also contain antibodies to the same target, although it may bind to a different epitope on the antigen. The test line will show as a colored band in positive samples, resulting from the accumulation or capture of antibody-bearing colored particles. In some embodiments, the lateral flow immunoassay can be a double antibody sandwich assay, a competitive assay, a quantitative assay or variations thereof. Conventional competitive LFIAs are similar to competitive ELISA. The sample first encounters colored particles which are labeled with the target antigen or an analogue. The test line contains antibodies to the target/its analogue. Unlabeled antigen in the sample will block the binding sites on the antibodies preventing capture of the colored particles at the test line. The test line will show as a colored band in negative samples. There are a number of variations on lateral flow technology. It is also possible to apply multiple capture zones to create a multiplex test.

Detection Reagents

Any substance generally capable of producing a signal that is detectable visually or by an instrumental device can be used as a detection reagent. Suitable detectable substances can include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances are described in U.S. Pat. No. 5,670,381 to Jou, et al. and U.S. Pat. No. 5,252,459 to Tarcha, et al., which are incorporated herein in their entirety by reference. If the detectable substance is colored, the ideal electromagnetic radiation is light of a complementary wavelength. For instance, blue detection probes strongly absorb red light.

In some embodiments, the detectable substance can be a luminescent compound that produces an optically detectable signal. For example, suitable fluorescent molecules can include, but are not limited to, fluorescein, europium chelates, phycobiliprotein, rhodamine, and their derivatives and analogs. Other suitable fluorescent compounds are semiconductor nanocrystals commonly referred to as "quantum dots."

In another embodiment, the detection agent is a particle. Examples of particles useful in the methods, assays and kits described herein include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads.

Further, suitable phosphorescent compounds can include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex can contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and II, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference.

Bipyridine metal complexes can also be utilized as phosphorescent compounds. Some examples of suitable bipyridine complexes include, but are not limited to, bis[(4,4'-carbomethoxy)-2,2'-bipyridine]2-[3-(4-methyl-2,2'-bipyridine-4-yl)propyl]-1,3-dioxolane ruthenium OD; bis(2, 2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2, 2'bipyridine)ruthenium (II); (2,2'-bipyridine) [bis-bis(1,2-diphenylphosphino)ethylene]2-[3-(4-methyl-2,2'-bipyridine-4'-yl)propyl]-1,3-dioxolane osmium (II); bis(2, 2'-bipyridine)[4-(4'-methyl-2,2'-bipyridine)-butylamine] ruthenium (II); bis(2,2'-bipyridine)[1-bromo-4(4'-methyl-2, 2'-bipyridine-4-yl)butane]ruthenium OD; bis(2,2'-bipyridine)maleimidohexanoic acid, 4-methyl-2,2'-bipyridine-4'-butylamide ruthenium (II), and so forth.

Additional Immunoassays

An immunoassay is a biochemical test that measures the concentration of a substance in a biological sample, typically a fluid sample, using the interaction of an antibody or antibodies to its antigen. The assay takes advantage of the highly specific binding of an antibody with its antigen. In some embodiments, specific binding of a UDP molecule with an anti-UDP antibody forms a UDP-antibody complex. The complex can then be detected by a variety of methods known in the art. An immunoassay also often involves the use of a detection antibody. Antibodies contemplated for use with the methods and assays described herein include an anti-UDP-glucose antibody, an anti-UDP antibody, and anti-UDP-glucuronic acid antibody. Such antibodies can be designed and generated using methods known in the art and/or described herein.

In one embodiment, the antibody is detectably labeled or capable of generating a detectable signal. In one embodiment, the antibody is fluorescently labeled.

In some embodiments, levels of a desired biomarker or analyte (e.g., UDP-glucose, UDP etc.) are measured by ELISA, also called enzyme immunoassay or EIA. ELISA is a biochemical technique that detects the presence of an antibody or an antigen in a sample.

In one embodiment, an ELISA involving at least one antibody with specificity for the particular desired antigen can be performed. A known amount of sample and/or antigen is immobilized on a solid support (e.g., a polystyrene micro titer plate). Immobilization can be either non-specific (e.g., by adsorption to the surface) or specific (e.g., where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample.

Older ELISAs utilize chromogenic substrates, though newer assays employ fluorogenic substrates with much higher sensitivity.

In one embodiment, a sandwich ELISA is used, where two antibodies specific for the target can be used. There are other different forms of ELISA, which are well known to those skilled in the art. Standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904.

Antibodies and Production Thereof

Suitable antibodies for use with the methods and assays described herein include, but are not limited to, polyclonal, monoclonal, chimeric, humanized, recombinant, single chain, $F_{ab}$, $F_a t$, $F_{sc}$, $Pv_v$, and $F_{(ab')2}$ fragments.

General techniques for production of mouse, rat, rabbit or even human antibodies are known in the art and/or are described herein. It is contemplated that any mammalian subject human hybridoma cell lines that produce a monoclonal antibody. Typically, the host animal is inoculated intraperitoneally, intramuscularly, orally, subcutaneously, intraplantar, and/or intradermally with an amount of immunogen, including as described herein.

Hybridomas can be prepared from lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to: X63-Ag8.653 and those from the Salk Institute, Cell Distribution Center, San Diego, Calif., USA, can be used in the hybridization. Generally, the technique involves fusing myeloma cells and lymphoid cells using a fusogen such as polyethylene glycol, or by electrical means known to those skilled in the art. After the fusion, the cells are separated from the fusion medium and grown in a selective growth medium, such as hypoxanthine-aminopterin-thymidine (HAT) medium, to eliminate unhybridized parent cells. As another alternative to the cell fusion technique, EBV immortalized B cells can be used to produce monoclonal antibodies to a desired analyte as described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that can be used as source of antibodies encompass all derivatives, progeny cells of the parent hybridomas that produce monoclonal antibodies capable of binding the desired analyte. Small, endogenously produced biomolecules may be difficult to raise antibodies to in an animal. However, it is contemplated that antibodies that specifically bind UDP-glucose or UDP, for example, can be raised with phage-display or other recombinant technology that uses at least partially randomized antibody sequences in a library expressed either in vitro or e.g., in bacterial cells, to select artificially generated antibodies for binding to UDP-glucose or UDP (see e.g., Scott, J. K. and Smith, G. P. (1990) *Science* 249: 386; "Phage display: A practical Approach", vol. 266, ed. Clackson and Lowman H, Oxford Univ. Press, 2004; "Phage Display: A laboratory Manual", Burton D R et al., CSHL Press, 2001 U.S. Pat. Nos. 5,702,892; 5,667,988; 5,759,817; 5,770,356; 5,658,727; 8,685,893; 7,811,973; 6,846,634; etc.).

If desired, an antibody (monoclonal or polyclonal) of interest (e.g., produced by a hybridoma or selected from a phage display library) can be sequenced and the polynucleotide sequence can then be cloned into a vector for expression or propagation. The sequence encoding the antibody of interest can be maintained in vector in a host cell and the host cell can then be expanded and frozen for future use. In an alternative, the polynucleotide sequence can be used for genetic manipulation to improve the affinity (affinity maturation), or other characteristics of the antibody. It will be apparent to one of skill in the art that one or more polynucleotide changes can be made to the antibody and still maintain its binding specificity to the target antigen.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Genetically engineered antibodies, such as humanized antibodies, chimeric antibodies, single-chain antibodies, and bi-specific antibodies, can be produced via, e.g., conventional recombinant technology. In one example, DNA encoding a monoclonal antibody specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA can be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen. Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to a desired antigen can be identified from the library following routine procedures. Positive clones can be subjected to further screening to identify those that bind the desired analyte.

Automated Assays

In one aspect, the assays described herein can be adapted to be performed onan automated device platform that is programmed to automatically add, transfer and optionally, mix liquid samples or reaction mixtures, for example, in wells of a multiwell plate. The wells can include reagents as necessary, either added in liquid/solution form or, for example, dried or immobilized on a surface within the wells. Automated platforms that include liquid handling modules as well as detection (e.g., fluorescence, luminescence, absorbance, reflectance, etc.) modules are known to those of skill in the art. As but one non-limiting example, one might use, e.g., a Beckman Coulter AU5800 device. When adapted to an automated design, multiwall plates can include, in addition to test wells for assaying an unknown test sample, control wells including, e.g., blanks lacking enzyme or other reagents, to permit, among other things, the determination of background levels of, e.g., intermediate or surrogate indicator NADH. Other controls can include, e.g., positive control wells including a known amount of UDP-glucose; a set of separate positive control wells can include varying known amounts of UDP-glucose to establish a standard curve, e.g., over one or a plurality of orders of magnitude, that is read by the device and used to calculate amounts of UDP-glucose in the unknown test samples.

Methods of Treating a Disease

Also provided herein are methods of treating a disease following diagnosis or prognosis with an assay/method as described herein. That is, treatment for a disease can be initiated following the detection of an undesirable modulation in the level of UDP-glucose in a sample. In some embodiments, such as in renal inflammation or lung disorders (e.g., asthma, cystic fibrosis, chronic obstructive pulmonary disease), levels of UDP-glucose are increased. In other embodiments, such as in gastric cancer, UDP-glucose levels are reduced. Also contemplated herein is the use of this assay and/or method as a companion diagnostic with a particular therapeutic agent.

In some embodiments, when the subject is identified as having renal inflammation, the assay or method further comprises administering to the subject a treatment appropriate for treating renal inflammation. Renal inflammation, also called nephritis, can include several types such as glomerulonephritis, membranoproliferative glomerulonephritis, interstitial nephritis, IgA nephropathy, pyelonephritis, autoimmune disorders related to CKD and inflammation, lupus nephritis, Goodpasture's syndrome, and Wegener's granulomatosis.

In some embodiments, the therapeutic agent is a small or large organic or inorganic molecule. As used herein, the term "small molecule" refers to natural or synthetic molecules having a molecular mass of less than about 5 kD, organic or inorganic compounds having a molecular mass of less than about 5 kD, less than about 2 kD, or less than about 1 kD.

In some embodiments, the therapeutic agent can be an engineered cell, an antibody molecule or an antigen-binding fragment thereof. Suitable antibodies include, but are not limited to, polyclonal, monoclonal, chimeric, humanized, recombinant, single chain, $F_{ab}$, $F_a t$, $F_{sc}$, $Pv_v$, and $F_{(ab')2}$ fragments.

The term "effective amount" as used herein refers to the amount of a therapy needed to alleviate at least one or more symptoms of the disease or disorder (e.g., inflammation, gastric cancer, lung disorders or renal inflammation), and relates to a sufficient amount of a therapeutic composition to provide the desired effect. The term "therapeutically effective amount" therefore refers to an amount of a therapy that is sufficient to cause a particular effect when administered to a typical subject. An effective amount as used herein, in various contexts, would also include an amount sufficient to delay the development of a symptom of the disease, alter the course of a symptom of the disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

In some embodiments, an effective amount of a therapeutic composition can be determined using repeated testing using the assays and methods described herein and determining if UDP-glucose levels are normalizing or normalized. In some embodiments, an effective amount of a therapeutic composition can be an amount that decreases or increases the amount of UDP-glucose in a sample (e.g., urine) obtained from a subject by a statistically significant amount.

In some embodiments, an effective amount of a therapeutic composition can be an amount which reduces the extent of renal inflammation. In some embodiments, an effective amount of a therapeutic agent can be an amount that decreases the expression or level of pro-inflammatory chemokines in ICs. In some embodiments, an effective amount of a therapeutic composition can be an amount that reduces the growth of a gastric cancer or that reduces symptom(s) of a lung disorder, such as asthma, cystic fibrosis or chronic obstructive pulmonary disease (COPD).

The dosage can be determined by one of skill in the art and can also be adjusted by the individual physician in the event of any complication. Typically, the dosage of a composition comprising a therapeutic agent can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, or from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, or from 4.5 g/kg body weight to 5 g/kg body weight. Effective doses may be extrapolated from dose-response curves derived from in vitro or animal model test bioassays or systems. The dosage should not be so large as to cause unacceptable adverse side effects.

In some embodiments, the therapeutic agent can improve renal function or lung function. For example, renal or lung function is improved by at least 10%, at least 20%, at least 30%, at least 40%, at least 50%, at least 60%, at least 70%, at least 80%, at least 90%, at least 100%, at least 200%, or at least 300%. Measurable markers of renal function, are well known in the medical and veterinary literature and to those of skill in the art, and include, but are not limited to, blood urea nitrogen or "BUN" levels (both static measurements and measurements of rates of increase or decrease in BUN levels), serum creatinine levels (both static measurements and measurements of rates of increase or decrease in serum creatinine levels), measurements of the BUN/creatinine ratio (static measurements of measurements of the rate of change of the BUN/creatinine ratio), urine/plasma ratios for creatinine, urine/plasma ratios for urea, glomerular filtration rates (GFR), serum concentrations of sodium ($Na^+$), urine osmolarity, daily urine output, and the like. Of the above, measurements of the plasma concentrations of creatinine and/or urea or BUN are particularly important and useful readouts of renal function. Measurable markers of lung function can include: spirometry, gas diffusion, body plethysmography, inhalation challenge test and/or an exercise stress test.

EXAMPLES

Example 1

UDP-Glucose Dehydrogenase Coupled to NADH

The present disclosure relates to the design of novel assays and methods for the detection of the pro-inflammatory molecule UDP-glucose (UDPG) in a sample from a subject, such as a urine sample. Other fluids such as serum or others described elsewhere herein can also be analyzed using these methods. Several methods (including enzymatic- and immuno-assay) are described herein, and each method can use one or more of several detection modalities (e.g., colorimetric, luminescence, fluorescence detection techniques) and devices (multi-chamber plate liquid assay, lateral flow "dipstick" assay).

While the assays described herein can provide information on UDP-glucose levels in samples from any individual, a target population includes hospitalized patients, including but not limited to critically ill patients, intensive care unit (ICU) patients, and septic, multi-trauma and transplant patients.

Further, provided herein are means to quantify the amount of UDP-glucose (UDPG) by converting it into UDP-glucuronic (UDP-GlA) acid and NADH, via the enzyme UDP-glucose dehydrogenase (UDPGD). For every unit of UDPG converted to UDP-GlA, two units of NADH are produced:

$$UDPG + 2NAD^+ \xrightarrow{UDPG} UDP\text{-}GlA + 2NADH \quad \text{Equation 1}$$

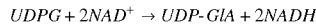

UDPGD is highly selective for UDP-G and $NAD^+$ is a co-factor in this reaction.

NADH production can be measured by many different techniques, which allows for a broad adaptability of this assay. For example, NADH can be measured by colorimetric, luminescence, or fluorescence techniques. The assay and methods described herein can be performed using e.g., a multi-chamber plate liquid assay, or a lateral flow 'dipstick' assay. It is also contemplated herein that the assay can be adapted to an automated laboratory analyzer. The multi-chamber plate requires laboratory personnel to perform the test, and the results can be quantitative. A dipstick assay increases the ease of use, and allows it to be used at 'point-of-care' yet the results are generally semi-quantitative.

Prior to use, biological fluids can be processed by centrifugation or filtration to remove cells and debris. If starting NADH levels are high, they can be removed by heating in acidic conditions or by an enzymatic reaction. Fluids can be deproteinized with a 10 kD filter.

The following sets out an example protocol for a UDP-glucose assay adapted to a 96 well plate format. A schematic of a 96 well plate formatted for such an assay is shown in FIG. 1. The assay is a coupled enzyme assay with a luminescent read out, coupling two enzymatic reactions to measure UDP-glucose in the nanomolar range. The sample is urine, although other liquid biological samples can be used with adaptations evident to the ordinarily skilled user.

In this example, the UDP-glucose test system includes a UDP-glucose assay pre-processing system and a 96-well UDP-glucose assay system.

Pre-Processing System:

The pre-processing system includes a filter-syringe with a 10 kD molecular weight cut off through which urine is filtered into a Tris-HCl pH 8.5 buffer (Reagent A). The filter removes proteins from the urine to be tested; such proteins may inhibit the enzymatic reaction. The buffer standardizes all urines to the pH optimum of the reaction. Prior to the filtration step, urine samples are spun down to remove cells and cell debris. After these pre-processing steps, samples are ready for the enzymatic UDP-glucose detection assay, but can be stored frozen at $-80°$ C. until later use if desired or necessary.

UDP-Glucose Assay System:

As noted above, UDPGD catalyzes the stoichiometric reduction of $NAD^+$ to NADH when converting UDP-glucose to UDP-glucuronic acid. In this UDP-glucose assay system, NADH is then quantified by, e.g., a commercial luminescence assay (such as the assay sold under the trade name NAD/NADH-Glo Assay™, Promega), which cycles NADH back to $NAD^+$ and vice versa to amplify the luminescence.

UDP-Glucose Test Kit Protocol:

1. Pre-treated urine is added to the reaction wells within a multi-chamber plate (96-well). A drop of UDPGD (0.240 mg/mL*) is placed in the reaction well and NAD+ is added to a final concentration of 2 mM. The reaction described in Equation 1, above, is allowed to occur for a period of 10 minutes at room temperature (RT) for NADH production to take place from the conversion of UDP-glucose present in the fluids. In an alternative embodiment, the cofactor NAD+ can be present in the reaction wells in a dehydrated form to provide a final concentration of 2 mM.

(*enzyme activity requirements: One unit of enzyme is the amount of UDG-glucose dehydrogenase required to oxidize 1.0 □mole of UDP-glucose to UDP-glucuronic acid per minute at pH 8.7 at 25° C. The assay requires a minimum of $2.5 \times 10^{-6}$ units of enzyme per well, e.g., $3.0 \times 10^{-6}$ units, $5 \times 10^{-6}$ units, $1 \times 10^{-5}$ units, $1.5 \times 10^{-5}$ units, $2.0 \times 10^{-5}$ units, $2.5 \times 10^{-5}$ units, $5 \times 10^{-5}$ units, $7.5 \times 10^{-5}$ units, $1 \times 10^{-4}$ units, $2.5 \times 10^{-4}$ units, $5 \times 10^{-4}$ units, $7.5 \times 10^{-4}$ units, $1 \times 10^{-3}$ units, $2.5 \times 10^{-3}$ units, $5 \times 10^{-3}$ units, $7.5 \times 10^{-3}$ units, $1 \times 10^{-2}$ units, $2.5 \times 10^{-2}$ units, $5 \times 10^{-2}$ units or more. In one embodiment, 0.04 units of enzyme are added per well.)

2. After the 10-min reaction, UDPGD is removed. In one embodiment, the enzyme is removed by passing the solution through a 10K filter and placement into an empty well.

3. In an alternative embodiment, the UDPGD is immobilized in the reaction wells, such that by removing the liquid reacted sample, e.g., by pipetting to another well lacking the enzyme, the enzyme is removed from contact with the reacted sample. Methods for immobilizing enzyme within a well are known to those of skill in the art, and can involve active immobilization, e.g., through a cross-linker or via antibody capture, or passive immobilization, e.g., through ionic bonding to a polystyrene or other plastic plate surface.

4. Reagent B contains 0.4N NaOH, a strong base. Other strong bases as described herein can also be used. Reagent B is added to the well and the reaction is incubated for 15 minutes at 60-65° C. Heating in base decomposes the NAD+ reactant, but leaves the product NADH intact. In an alternative embodiment, Reagent B is already present in the well, e.g., in dried form; this has the advantage of decreasing the steps required by a technician or by an automated device.

5. Reagent C contains HCl/Trizma, an acidic buffer. Reagent C is added to the plate so that the fluid is neutralized for the subsequent reaction. As one example, the Trizma-HCl solution is a pH 7.5 solution prepared by 1:1 mixture of 0.4N HCl with 0.5M Trizma base. This can be added in a 1:1 ratio to the base-treated reaction mixture from step 4, e.g., 50 □l of alkalinized or base-treated reaction mixture is combined with 50 □l of the pH 7.5 Trizma-HCl solution to effect a final pH in the range of 7.5 to 8.0.
6. Reagent D contains a luciferin detection reagent, a reductase, a reductase substrate, an NAD cycling enzyme and NAD cycling substrate (e.g. Glow Reagent from Promega). Reagent D is added to the plate and generates light relative to the NADH concentration. The emitted light is read with a plate reader after a 30-60 minute incubation. The amplification of NADH coupled to luciferin detection is described in, e.g., Assay Drug Dev Technol. 2014 Dec. 1; 12(9-10): 514-526. doi: 10.1089/adt.2014.605; incorporated herein by reference.

For the assays described herein, in addition to the test wells, control wells for each urine sample can or should include a negative control well that lacks enzyme, and a positive control well spiked with a known quantity of UDP-glucose. In one embodiment, the assay includes on the plate a standard curve with known quantities of UDP-glucose in a set of control wells.

Figure 3B:
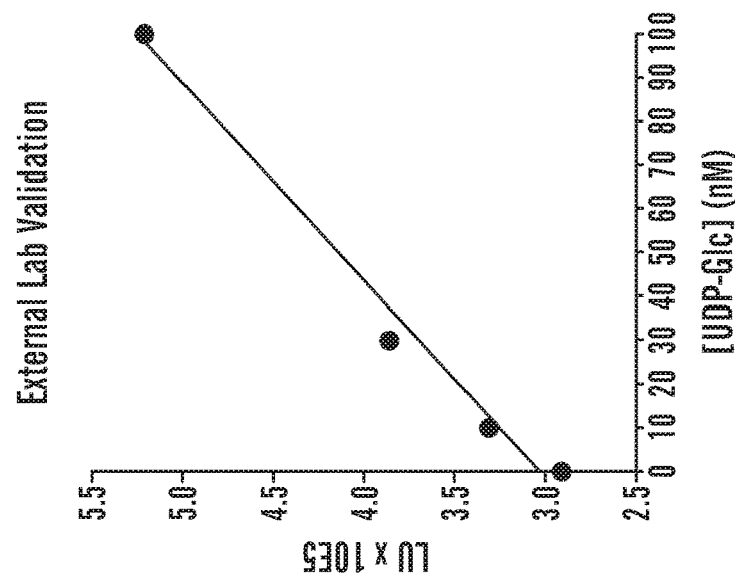
FIGS. 3A-3B show the reproducibility of a liquid phase UDP-glucose assay as described herein.
Figure 3A:
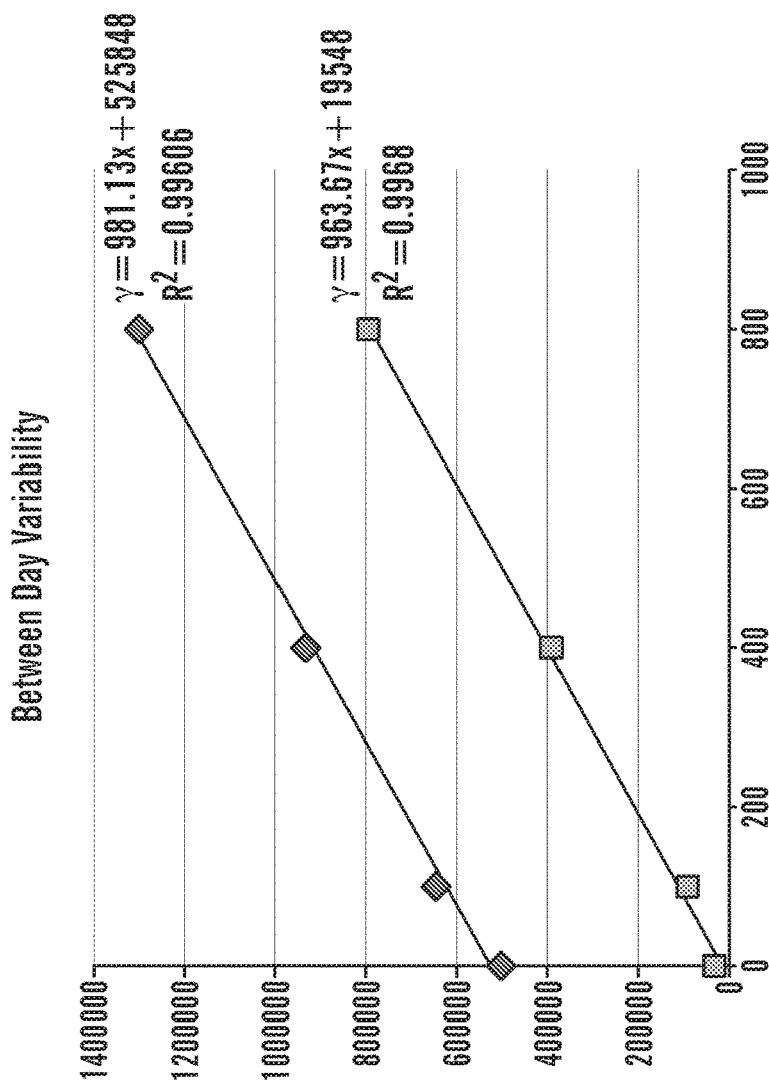

This dual enzymatic luminescence platform allows for highly sensitive detection of low UDP-glucose levels within the physiological range (0-400 nM). A linear relationship between UDP-glucose and the amount of emitted light is obtained. Standard curves in physiological buffer showed near identical slopes demonstrating consistent between day variability (FIG. 3A). Testing by an independent, external laboratory using current industry standard methods confirms accuracy of the UDPG dehydrogenase-mediated method described herein (FIG. 3B).

This assay can be performed by a technician or alternatively it can be adapted to an automated laboratory analyzer in a hospital lab.

An Exemplary Embodiment of a Lateral Flow Format

Figure 4:
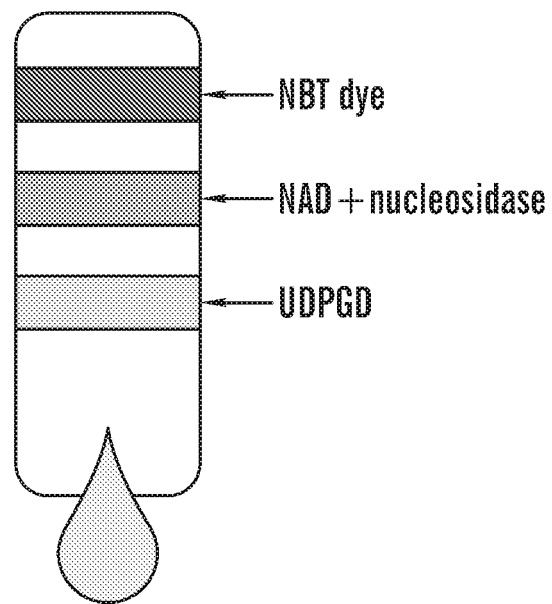
FIG. 4 is a schematic diagram of a exemplary dipstick format for measurement of NADH coupled to the conversion of UDP-glucose to UDP-glucuronic acid via the UDP-glucose dehydrogenase enzymatic reaction.

The assay described above can also be used in a 'dipstick' format using lateral flow technology (FIG. 4).
1. UDPGD is immobilized on a test region of a 'dipstick' or test strip.
2. UDPG containing biological fluid is buffered to pH 8-9 with Reagent A (50 mM Tris pH 8-9), and NAD+ is added to the sample prior to flow through. In an alternative embodiment, NAD+ is present on the device, e.g., in dried form.
3. The sample containing UDPG and NAD+ flows through the device by capillary action.
4. When the UDPG reaches the immobilized UDPGD test region, NADH is produced.
5. Passing through a high pH membrane then degrades the NAD+. In an alternate embodiment, NAD+ can be degraded by passing through an immobilized enzyme (NAD+ nucleosidase) that selectively degrades NAD+, leaving NADH intact.
6. NADH is quantified by coupling UDPG dependent NADH production to the reduction of a reporter dye or molecule, for example, nitro blue tetrazolium (NBT) (see e.g., FIG. 4). NBT forms an intensely colored precipitate upon reduction. Alternatively a luciferin reagent is bound to the dipstick. Upon NADH production, luciferin emits a light, which is detected by a dipstick luminometer. Alternatively a fluorescence detection agent is bound to the dipstick. Upon NADH production, fluorescence is produced and is detected by a dipstick fluorometer.

Example 3

Antibody Based Assays to Detect UDP-Glucose

Figure 5:
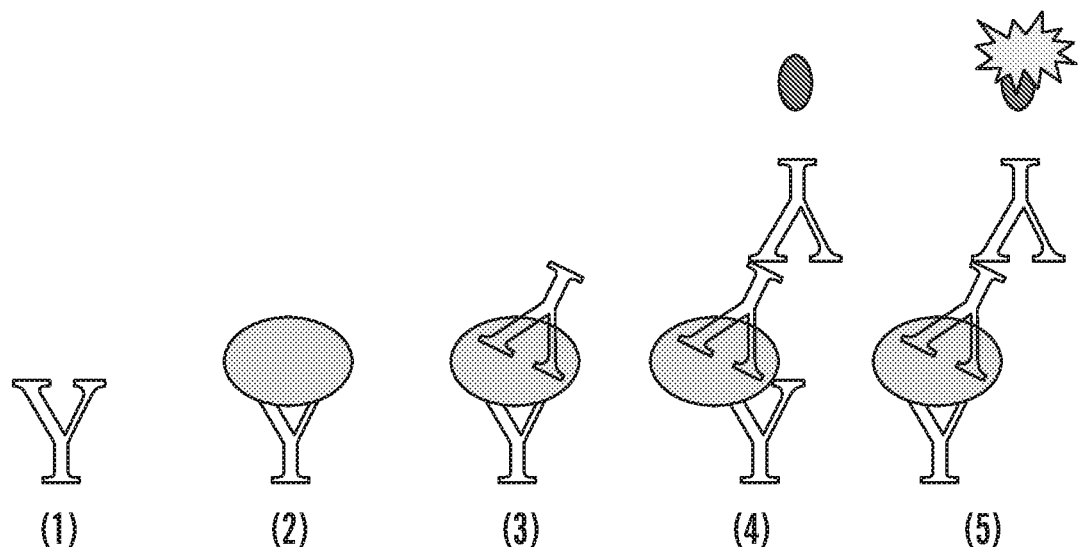
FIG. 5 is a schematic diagram showing, in one embodiment, the steps of a UDP-glucose (UDPG) ELISA assay. Step 1: Plate is coated with a capture antibody for UDPG; Step 2: Biological sample (e.g., urine sample) is added and any UDPG present binds to captured antibody; Step 3: a detection antibody is added, and binds to antigen; Step 4: Enyzme-Linked secondary antibody is added, and binds to the detecting antibody; Step 5: Substrate is added and is converted by enzyme to a detectable form (e.g., light, color, fluorescence).

Anti-UDPG antibody: This invention contemplates the detection of UDPG using an antibody-based assay. To do so, antibodies are raised against UDP-glucose itself. UDPG concentration can be measured using an enzyme linked immunosorbant assay (ELISA) in a multi-well plate or a lateral flow format (FIG. 5.)

An Exemplary Multi-Chamber Plate Format using Anti-UDPG Antibody
1. The UDPG-containing biological sample is added to a well of an ELISA plate containing an immobilized antibody against UDPG.
2. The well is washed to remove any unbound UDPG, and a secondary antibody bound to an enzyme is added.
3. The plate is washed to remove an unbound secondary antibody.
4. A detection reagent reacting with the enzyme linked to the secondary antibody is added and will result in the production of a color. Alternatively, a luminescence detection reagent can be used, which would result in the production of emitted light. Alternatively a fluorescence detection reagent can be used, which will result in the fluorescent emission when the plate is irradiated with light in the excitation wavelength for the produced fluorophore.
5. The amount of color or light is quantified by a plate reader.

An Exemplary Lateral Flow Format using Anti-UDPG Antibody

In the lateral flow format the solution containing UDPG flows through the test stick by capillary action.

When UDPG binds to an antibody immobilized on a 'test region' of the strip a detectable label accumulates.

The amount of dye accumulated can be read either by eye or using a digital test strip reader, for example, a smart phone test strip reader. Alternatively, a luciferin reagent is bound to the dipstick. Luciferin emits a light, which is detected by a dipstick luminometer. Alternatively, a fluorescence reagent is bound to the dipstick. Fluorescent light is emitted in response to light within the fluorophore excitation spectrum and detected by a dipstick fluorometer. Alternatively colloidal gold can be conjugated to the antibodies for a colorimetric measurement.

Anti-UDP antibody: Alternatively, an antibody against a byproduct of enzymatic UDPG conversion can be used to measure UDPG. This option provides a means to quantify UDPG by converting it into UDP and glycogen via the enzyme glycogen synthase. UDP production can be measured by ELISA in a multi-well plate or a lateral flow format, as described below:

Multi-Chamber Plate Format using Anti-UDP Antibody
1. The UDPG containing sample is incubated in the presence of glycogen synthase and any necessary co-factor proteins (such as glycogenin), resulting in UDP production.
2. The UDP containing solution is added to a well of an ELISA plate containing an immobilized antibody against UDP.
3. The well can be washed to remove any unbound UDP, and a secondary antibody bound to an enzyme is added.

4. The plate can be washed to remove an unbound secondary antibody.
5. A detection reagent will react with the enzyme linked to the secondary antibody and will result in the production of a color. Alternatively, a luminescence detection reagent will be used and will result in the production in the fluorescent emission when the plate is irradiated with light in the excitation wavelength for the produced fluorophore. Alternatively a fluorescence detection reagent will be used and will result in the production of fluorescent light. The amount of color or light can be quantified by a plate reader.

Lateral Flow Format using Anti-UDP Antibody

1. In the lateral flow format the solution containing UDP flows through the test stick by capillary action.
2. When UDP binds to an antibody immobilized on a 'test region' of the strip a detectable label accumulates.
3. The amount of accumulated label can be read either by eye or using a digital test strip reader, for example, a smart phone test strip reader. Alternatively a luciferin reagent is bound to the dipstick. Upon UDP production, luciferin emits a light, which is detected by a dipstick luminometer. Alternatively a fluorescence reagent is bound to the dipstick. Upon UDP production fluorescent light is emitted in response to light within the fluorophore excitation spectrum and is detected by a dipstick fluorometer. Alternatively colloidal gold can be conjugated to the antibodies for a colorimetric measurement.

REFERENCE

Eduardo R. Lazarowski, Deborah A. Shea, Richard C. Boucher, T. Kendal Harden. Release of Cellular UDP-glucose as a Potential Extracellular Signaling Molecule. *Mol Pharmacol.* 63: 1190-1197, 2003

The invention claimed is:

1. A method for measuring the presence or amount of uridine diphosphate glucose (UDP-glucose) in a sample, the method comprising:
    conducting an enzymatic reaction comprising contacting immobilized UDP-glucose dehydrogenase with a sample comprising UDP-glucose to form one or more UDP-glucose reaction products;
    removing the UDP-glucose dehydrogenase from contact with the sample; and
    measuring a level of the one or more UDP-glucose reaction products to thereby measure the presence or amount of UDP-glucose in the sample.

2. The method of claim 1, wherein the UDP-glucose dehydrogenase is immobilized in or on a solid support selected from the group consisting of a cell culture plate, a multiwell plate, a disc, a bead, a woven paper, a filter paper, cardboard, a well, a plate, an electrode, a coated test strip, an uncoated test strip, a lateral flow strip, a lateral flow device, a dipstick device, a particle, and a magnetic particle.

3. The method of claim 1, wherein the sample is a biological sample.

4. The method of claim 3, wherein the method further comprises removing protein(s) from the biological sample prior to the conducting step.

5. The method of claim 4, wherein the biological sample is urine, blood, or serum.

6. The method of claim 5, wherein the measuring step comprises using one selected from the group consisting of an antibody or fragment thereof, an ELISA, nitro blue tetrazolium (NBT), a luciferin reagent, a fluorescence detection agent, and a colloidal metal.

7. The method of claim 1, wherein at least one of the conducting step and the measuring step is conducted using a lateral flow device.

8. The method of claim 7, wherein the biological sample is from a subject having a disease, and wherein the method further comprises treating the subject with an agent when the presence or amount of UDP-glucose in the sample is modulated relative to a reference level.

9. The method of claim 8, wherein the subject is a critically ill patient, an intensive care unit (ICU) patient, a septic patient, a patient with multi-trauma, a transplant patient, an outpatient, a patient suspected of having the disease, a cardio-thoracic surgery patient, a major surgery patient, or an emergency room patient.

10. The method of claim 9, wherein the disease is renal inflammation, chronic kidney disease, acute kidney injury, asthma, cystic fibrosis, chronic obstructive pulmonary disease, or gastric cancer.

11. The method of claim 10, wherein the renal inflammation is selected from the group consisting of early stage renal inflammation, nephritis, acute tubular necrosis, glomerulonephritis, membranoproliferative glomerulonephritis, interstitial nephritis, IgA nephropathy, pyelonephritis, autoimmune disorders related chronic kidney disease, lupus nephritis, Goodpasture's syndrome, and Wegener's granulomatosis.

12. The method of claim 8, wherein the reference level comprises:
    an average level of UDP-glucose in a population of healthy subjects,
    a range of levels of UDP-glucose in a population of healthy subjects,
    two standard deviations above an average UDP-glucose level in a population of healthy subjects,
    a level of UDP-glucose in a sample obtained from the subject prior to onset of the disease or as early as possible after onset of the disease,
    a numeric value or range of values, or
    a colored scale provided by a test strip or dipstick manufacturer for comparison of the color obtained by applying a portion of the sample to the test strip or dipstick.

13. The method of claim 8, wherein the agent is a drug, a small molecule, a peptide, an antibody or fragment thereof, an engineered immune cell, an RNA interference agent, a nucleic acid, or a protein.

* * * * *

UNITED STATES PATENT AND TRADEMARK OFFICE
CERTIFICATE OF CORRECTION

| | | |
|---|---|---|
| PATENT NO. | : 11,034,992 B2 | Page 1 of 1 |
| APPLICATION NO. | : 16/087968 | |
| DATED | : June 15, 2021 | |
| INVENTOR(S) | : Breton et al. | |

It is certified that error appears in the above-identified patent and that said Letters Patent is hereby corrected as shown below:

In the Specification

At Column 1, Line 12:
Insert the following heading and paragraph:
--GOVERNMENT SUPPORT
This invention was made with government support under DK097124 awarded by the National Institutes of Health. The government has certain rights in the invention.--

Signed and Sealed this
Second Day of May, 2023

Katherine Kelly Vidal
*Director of the United States Patent and Trademark Office*